United States Patent
Mathias et al.

(10) Patent No.: US 11,083,841 B2
(45) Date of Patent: Aug. 10, 2021

(54) NEEDLE PROTECTOR, NEEDLE ASSEMBLY AND FLUID PROCESSING SET INCLUDING THE SAME

(75) Inventors: Jean-Marie Mathias, Lillois (BE); Daniel Lynn, Spring Grove, IL (US); Rich West, Lake Villa, IL (US); Tat Mui, Chicago, IL (US); Mark Jones, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 492 days.

(21) Appl. No.: 12/430,649

(22) Filed: Apr. 27, 2009

(65) Prior Publication Data

US 2009/0281506 A1  Nov. 12, 2009

Related U.S. Application Data

(63) Continuation-in-part of application No. 10/618,353, filed on Jul. 11, 2003, now Pat. No. 7,566,327.
(Continued)

(51) Int. Cl.
*A61M 5/162* (2006.01)
*A61B 5/15* (2006.01)
(Continued)

(52) U.S. Cl.
CPC ..... *A61M 5/1626* (2013.01); *A61B 5/150534* (2013.01); *A61B 5/150633* (2013.01);
(Continued)

(58) Field of Classification Search
CPC .... A61M 5/321; A61M 5/3243; A61M 5/158; A61M 5/162; A61M 5/1626;
(Continued)

(56) References Cited

U.S. PATENT DOCUMENTS 2,857,912 A   10/1958  Feinstone et al.
3,323,523 A    6/1967  Scislowicz et al.
(Continued)

FOREIGN PATENT DOCUMENTS

CA      729419     3/1966
EP    0 265 159 A2  4/1988
(Continued)

OTHER PUBLICATIONS

Abstract of Japanese Patent Application No. 63-036413 (JP 8836413), filed Feb. 18, 1988.
(Continued)

*Primary Examiner* — Shefali D Patel
(74) *Attorney, Agent, or Firm* — Cook Alex Ltd.

(57) ABSTRACT

Needle protector assemblies including needle assemblies and needle protectors for housing used blood collection needles are disclosed. The needle protectors are single-piece protectors that include an open distal end for receiving a needle hub (with a needle mounted thereon). A retaining member locks the needle hub when the needle hub is substantially retracted. A stop engages the needle hub in a fully retracted position such that a needle post is completely contained within an interior chamber of the needle protectors. A viewing slot in the needle protectors is provided.

19 Claims, 7 Drawing Sheets

Related U.S. Application Data

(60) Provisional application No. 60/402,286, filed on Aug. 9, 2002.

(51) Int. Cl.
   | | |
   |---|---|
   | *A61B 50/30* | (2016.01) |
   | *A61M 5/158* | (2006.01) |
   | *A61M 25/06* | (2006.01) |
   | *A61B 5/153* | (2006.01) |
   | *A61M 5/32* | (2006.01) |

(52) U.S. Cl.
   CPC .... *A61B 5/150641* (2013.01); *A61B 50/3001* (2016.02); *A61M 5/158* (2013.01); *A61M 25/0612* (2013.01); *A61M 25/0631* (2013.01); *A61B 5/153* (2013.01); *A61B 5/15003* (2013.01); *A61B 5/150259* (2013.01); *A61B 5/150389* (2013.01); *A61B 5/150503* (2013.01); *A61B 5/150717* (2013.01); *A61B 5/150809* (2013.01); *A61B 5/150824* (2013.01); *A61M 5/3243* (2013.01); *A61M 2005/3247* (2013.01)

(58) Field of Classification Search
   CPC ...... A61M 2005/1587; A61M 25/0612; A61M 25/0631; A61B 50/3001; A61B 5/150534; A61B 5/150633; A61B 5/150641; A61B 5/150717
   USPC ..... 604/171, 192, 198, 263, 164.01, 164.04, 604/164.07, 110, 158, 159, 162
   See application file for complete search history.

(56) References Cited

U.S. PATENT DOCUMENTS

| | | | |
|---|---|---|---|
| 3,523,530 A * | 8/1970 | Pagones | A61M 5/158 604/263 |
| 3,568,673 A | 3/1971 | Cowley | |
| 3,572,334 A | 3/1971 | Petterson | |
| 3,595,230 A | 7/1971 | Suyeoka et al. | |
| 3,610,240 A | 10/1971 | Harautuneian | |
| RE27,797 E | 10/1973 | Sorenson et al. | |
| 3,910,272 A | 10/1975 | Forberg | |
| 4,068,659 A | 1/1978 | Moorehead | |
| 4,170,993 A | 10/1979 | Alvarez | |
| 4,222,379 A | 9/1980 | Smith | |
| 4,329,989 A | 5/1982 | Daltons et al. | |
| 4,417,887 A | 11/1983 | Koshi | |
| 4,425,120 A | 1/1984 | Sampson et al. | |
| 4,573,976 A | 3/1986 | Sampson et al. | |
| 4,631,057 A | 12/1986 | Mitchell | |
| 4,631,058 A | 12/1986 | Raines | |
| 4,643,722 A | 2/1987 | Smith, Jr. | |
| 4,664,654 A | 5/1987 | Strauss | |
| 4,676,783 A * | 6/1987 | Jagger | A61M 25/0631 604/162 |
| 4,693,708 A | 9/1987 | Wanderer et al. | |
| 4,731,059 A | 3/1988 | Wanderer et al. | |
| 4,735,618 A | 4/1988 | Hagen | |
| 4,737,143 A | 4/1988 | Russell | |
| 4,747,836 A | 5/1988 | Luther | |
| 4,790,828 A | 12/1988 | Dombrowski et al. | |
| 4,820,282 A | 4/1989 | Hogan | |
| 4,840,613 A | 6/1989 | Balbierz | |
| 4,840,619 A | 6/1989 | Hughes | |
| 4,842,587 A | 6/1989 | Poncy | |
| 4,867,172 A | 9/1989 | Haber et al. | |
| 4,874,383 A | 10/1989 | McNaughton | |
| 4,888,001 A | 12/1989 | Schoenberg | |
| 4,917,243 A | 4/1990 | Abrams et al. | |
| 4,917,660 A | 4/1990 | Speller, Jr. et al. | |
| 4,923,445 A | 5/1990 | Ryan | |
| 4,927,019 A | 5/1990 | Haber et al. | |
| 4,927,415 A | 5/1990 | Brodsky | |
| 4,929,241 A | 5/1990 | Kulli | |
| 4,932,940 A | 6/1990 | Walker et al. | |
| 4,935,011 A | 6/1990 | Hogan | |
| 4,935,012 A | 6/1990 | Magre et al. | |
| 4,941,881 A | 7/1990 | Masters et al. | |
| 4,943,283 A | 7/1990 | Hogan | |
| 4,943,284 A | 7/1990 | Erlich | |
| 4,946,447 A | 8/1990 | Hardcastle et al. | |
| 4,994,046 A | 2/1991 | Wesson et al. | |
| 5,013,305 A | 5/1991 | Opie et al. | |
| 5,030,212 A | 7/1991 | Rose | |
| 5,061,250 A | 10/1991 | Shields | |
| 5,067,490 A | 11/1991 | Haber | |
| 5,069,341 A | 12/1991 | Barbieri et al. | |
| 5,085,639 A | 2/1992 | Ryan | |
| 5,086,780 A | 2/1992 | Schmitt | |
| 5,088,982 A | 2/1992 | Ryan | |
| 5,092,461 A | 3/1992 | Adam | |
| 5,098,403 A | 3/1992 | Sampson | |
| 5,108,376 A | 4/1992 | Bonaldo | |
| 5,112,311 A | 5/1992 | Utterberg et al. | |
| 5,112,313 A | 5/1992 | Sallee | |
| 5,120,320 A | 6/1992 | Fayngold | |
| 5,137,515 A | 8/1992 | Hogan | |
| 5,137,519 A | 8/1992 | Littrell et al. | |
| 5,154,698 A | 10/1992 | Compagnucci et al. | |
| 5,156,599 A | 10/1992 | Ranford et al. | |
| 5,167,640 A | 12/1992 | Balding | |
| 5,169,392 A | 12/1992 | Ranford et al. | |
| 5,171,231 A | 12/1992 | Heiliger | |
| 5,176,650 A | 1/1993 | Haining | |
| 5,188,119 A | 2/1993 | Sunderland | |
| 5,192,275 A * | 3/1993 | Burns | A61M 25/0631 604/177 |
| 5,197,956 A | 3/1993 | Brizuela | |
| RE34,223 E | 4/1993 | Bonaldo | |
| 5,201,713 A | 4/1993 | Rossetti | |
| 5,215,528 A | 6/1993 | Purdy et al. | |
| 5,219,339 A * | 6/1993 | Saito | A61M 25/0637 604/177 |
| 4,840,613 B1 | 7/1993 | Balbierz | |
| 5,226,894 A | 7/1993 | Haber et al. | |
| 5,242,417 A | 9/1993 | Paudler | |
| 5,266,072 A | 11/1993 | Utterberg et al. | |
| 5,279,588 A | 1/1994 | Nicoletti et al. | |
| 5,290,255 A | 3/1994 | Vallelunga et al. | |
| 5,290,264 A | 3/1994 | Utterberg | |
| 5,312,359 A | 5/1994 | Wallace | |
| 5,312,368 A | 5/1994 | Haynes | |
| 5,330,438 A | 7/1994 | Gollobin et al. | |
| 5,346,475 A | 9/1994 | Gregorio | |
| 5,350,368 A | 9/1994 | Shields | |
| D353,456 S | 12/1994 | Fayngold et al. | |
| 5,376,075 A | 12/1994 | Haughton et al. | |
| 5,380,293 A | 1/1995 | Grant | |
| 5,382,240 A * | 1/1995 | Lam | 604/177 |
| 5,401,250 A | 3/1995 | Shields | |
| 5,425,720 A | 6/1995 | Rogalsky et al. | |
| 5,429,612 A | 7/1995 | Berthier | |
| 5,429,613 A | 7/1995 | D'Amico | |
| 5,433,703 A | 7/1995 | Utterberg et al. | |
| 5,445,629 A | 8/1995 | Debrauwere et al. | |
| 5,486,163 A | 1/1996 | Haynes | |
| 5,495,855 A | 3/1996 | Dudar et al. | |
| 5,498,241 A | 3/1996 | Fabozzi | |
| 5,498,244 A | 3/1996 | Eck | |
| 5,498,245 A | 3/1996 | Whisson | |
| 5,501,672 A | 3/1996 | Firth et al. | |
| 5,505,711 A | 4/1996 | Arakawa et al. | |
| 5,520,654 A | 5/1996 | Wahlberg | |
| 5,545,146 A | 8/1996 | Ishak | |
| 5,549,558 A | 8/1996 | Martin | |
| 5,549,571 A | 8/1996 | Sak | |
| 5,549,572 A | 8/1996 | Byrne et al. | |
| 5,554,130 A * | 9/1996 | McDonald | A61M 5/3271 600/576 |
| 5,562,636 A | 10/1996 | Utterberg | |
| 5,562,637 A | 10/1996 | Utterberg | |

(56) References Cited

U.S. PATENT DOCUMENTS

| | | | |
|---|---|---|---|
| 5,573,512 A | 11/1996 | Van den Haak |
| 5,584,813 A | 12/1996 | Livingston et al. |
| 5,601,536 A | 2/1997 | Crawford et al. |
| 5,643,220 A | 7/1997 | Cosme |
| 5,672,160 A | 9/1997 | Osterlind et al. |
| 5,672,161 A | 9/1997 | Allen et al. |
| 5,681,295 A | 10/1997 | Gyure et al. |
| 5,693,022 A | 12/1997 | Haynes |
| 5,704,917 A | 1/1998 | Utterberg |
| 5,704,920 A | 1/1998 | Gyure et al. |
| 5,704,924 A | 1/1998 | Utterberg et al. |
| 5,718,688 A | 2/1998 | Wozencroft |
| 5,735,827 A | 4/1998 | Adwers |
| 5,746,215 A * | 5/1998 | Manjarrez .................. 600/573 |
| 5,746,718 A | 5/1998 | Steyn |
| 5,749,859 A | 5/1998 | Powell |
| 5,772,638 A | 6/1998 | Utterberg et al. |
| 5,795,339 A | 8/1998 | Erskine |
| 5,800,400 A | 9/1998 | Hogan |
| 5,810,775 A | 9/1998 | Shaw |
| 5,817,064 A | 10/1998 | DeMarco et al. |
| 5,827,239 A | 10/1998 | Dillon et al. |
| 5,833,670 A | 11/1998 | Dillon et al. |
| 5,846,227 A | 12/1998 | Osterlind |
| 5,851,196 A | 12/1998 | Arnett |
| 5,879,337 A | 3/1999 | Kuracina et al. |
| 5,891,098 A | 4/1999 | Huang |
| 5,891,099 A | 4/1999 | Nakajima et al. |
| 5,897,508 A | 4/1999 | Konrad |
| 5,899,886 A | 5/1999 | Cosme |
| 5,910,132 A | 6/1999 | Schultz |
| 5,925,032 A | 7/1999 | Clements |
| 5,951,523 A | 9/1999 | Osterlind et al. |
| 5,951,529 A | 9/1999 | Utterberg |
| 6,013,059 A | 1/2000 | Jacobs |
| 6,042,570 A | 3/2000 | Bell et al. |
| 6,093,170 A | 7/2000 | Hsu et al. |
| 6,120,482 A | 9/2000 | Szabo |
| 6,165,157 A | 12/2000 | Dillon et al. |
| 6,193,694 B1 * | 2/2001 | Bell .................. A61M 25/0631 604/163 |
| 6,200,294 B1 | 3/2001 | Liu |
| 6,210,371 B1 * | 4/2001 | Shaw .................. 604/164.08 |
| 6,210,373 B1 | 4/2001 | Allmon |
| 6,235,005 B1 | 5/2001 | Chang et al. |
| 6,235,006 B1 * | 5/2001 | Dillon .................. A61M 25/0631 604/162 |
| 6,238,375 B1 | 5/2001 | Powell |
| 6,287,278 B1 | 9/2001 | Woehr et al. |
| 6,293,925 B1 | 9/2001 | Safabash et al. |
| D449,687 S | 10/2001 | Hommann et al. |
| 6,302,868 B1 | 10/2001 | Mohammad |
| 6,309,376 B1 | 10/2001 | Alesi |
| 6,319,233 B1 | 11/2001 | Jansen |
| 6,325,781 B1 | 12/2001 | Takagi et al. |
| 6,328,713 B1 | 12/2001 | Hollister |
| 6,332,875 B2 | 12/2001 | Inkpen et al. |
| 6,355,021 B1 | 3/2002 | Nielsen et al. |
| 6,387,086 B2 | 5/2002 | Mathias et al. |
| 6,406,454 B1 * | 6/2002 | Hajianpour .......... A61M 1/0039 210/106 |
| 6,416,323 B1 | 7/2002 | Grenfell et al. |
| 6,527,115 B2 | 3/2003 | Rabiner et al. |
| 6,540,696 B1 | 4/2003 | Dillon et al. |
| D476,419 S | 6/2003 | Swenson |
| 6,632,201 B1 | 10/2003 | Mathias et al. |
| D491,661 S | 6/2004 | Ringstrom |
| 6,846,302 B2 | 1/2005 | Shemesh et al. |
| 6,908,455 B2 * | 6/2005 | Hajianpour .................. 604/266 |
| 6,972,002 B2 | 12/2005 | Thorne |
| 6,976,976 B2 | 12/2005 | Doyle |
| 6,997,913 B2 | 2/2006 | Wilkinson |
| 7,044,941 B2 | 5/2006 | Mathias et al. |
| 7,060,055 B2 | 6/2006 | Wilkinson et al. |
| 7,097,636 B2 | 8/2006 | Pessin |
| 7,101,355 B2 | 9/2006 | Doyle |
| 7,112,187 B2 | 9/2006 | Karlsson |
| 7,189,217 B2 | 3/2007 | Chang et al. |
| 7,201,736 B2 | 4/2007 | Hauri |
| D543,273 S | 5/2007 | Young et al. |
| 7,270,649 B2 | 9/2007 | Fitzgerald |
| 7,276,049 B2 | 10/2007 | Bang et al. |
| 7,300,420 B2 | 11/2007 | Doyle |
| D560,798 S | 1/2008 | Hosoda et al. |
| 7,341,573 B2 | 3/2008 | Ferguson et al. |
| 7,357,783 B2 | 4/2008 | Millerd |
| 7,357,784 B2 | 4/2008 | Ferguson |
| 7,566,327 B2 * | 7/2009 | Mathias .................. 604/263 |
| 2001/0016714 A1 | 8/2001 | Bell et al. |
| 2002/0161338 A1 | 10/2002 | Peterson |
| 2003/0093035 A1 | 5/2003 | Mohammed |
| 2003/0125677 A1 | 7/2003 | Swenson et al. |
| 2003/0132131 A1 | 7/2003 | Rabiner et al. |
| 2003/0135157 A1 | 7/2003 | Saulenas et al. |
| 2003/0176813 A1 | 9/2003 | Mathias et al. |
| 2003/0187402 A1 | 10/2003 | Doyle |
| 2003/0195475 A1 | 10/2003 | Ferguson et al. |
| 2003/0220617 A1 | 11/2003 | Dickerson |
| 2004/0106905 A1 | 6/2004 | Jansen et al. |
| 2004/0127857 A1 | 7/2004 | Shemesh et al. |
| 2004/0260325 A1 | 12/2004 | Kuhr et al. |
| 2005/0004552 A1 | 1/2005 | Barrelle |
| 2005/0020979 A1 | 1/2005 | Westbye et al. |
| 2005/0020985 A1 | 1/2005 | Doyle |
| 2005/0021066 A1 | 1/2005 | Kuhr et al. |
| 2005/0033242 A1 | 2/2005 | Perez et al. |
| 2005/0054987 A1 | 3/2005 | Perez et al. |
| 2005/0065467 A1 | 3/2005 | Pudelko et al. |
| 2005/0096597 A1 | 5/2005 | Crawford et al. |
| 2005/0096601 A1 | 5/2005 | Doyle |
| 2005/0107740 A1 | 5/2005 | Jensen et al. |
| 2005/0182363 A1 | 8/2005 | Kulli |
| 2006/0021890 A1 | 2/2006 | Wang |
| 2006/0032769 A1 | 2/2006 | Erickson et al. |
| 2006/0074384 A1 | 4/2006 | Kohler |
| 2006/0157363 A1 | 7/2006 | Abidin et al. |
| 2006/0173414 A1 | 8/2006 | Buetikofer et al. |
| 2006/0229569 A1 | 10/2006 | Lavi et al. |
| 2006/0264825 A1 | 11/2006 | Westbye et al. |
| 2006/0282044 A1 | 12/2006 | Mohammed |
| 2007/0021720 A1 | 1/2007 | Guillermo |
| 2007/0078409 A1 | 4/2007 | Saltz |
| 2007/0129686 A1 | 6/2007 | Daily et al. |
| 2007/0191777 A1 | 8/2007 | King |
| 2007/0233000 A1 | 10/2007 | Perez |
| 2007/0233010 A1 | 10/2007 | Perez |
| 2007/0244438 A1 * | 10/2007 | Perez .................. A61M 25/0631 604/164.01 |
| 2007/0250014 A1 | 10/2007 | Utterberg et al. |
| 2007/0282275 A1 | 12/2007 | Ferguson et al. |
| 2008/0011640 A1 | 1/2008 | Cervantes |
| 2008/0015513 A1 | 1/2008 | Westbye et al. |
| 2008/0021409 A1 | 1/2008 | Pessin |
| 2008/0051725 A1 | 2/2008 | Bang et al. |
| 2008/0071222 A1 | 3/2008 | Rhad et al. |
| 2008/0097343 A1 | 4/2008 | Woehr |
| 2008/0097345 A1 | 4/2008 | Ferguson |
| 2009/0187153 A1 | 7/2009 | West et al. |
| 2012/0097759 A1 | 4/2012 | Vigne |

FOREIGN PATENT DOCUMENTS

| | | |
|---|---|---|
| EP | 0 353 916 A1 | 7/1990 |
| EP | 0 425 448 A2 | 2/1991 |
| EP | 0 459 953 A1 | 4/1991 |
| EP | 0 425 448 B1 | 5/1991 |
| EP | 0 459 953 B1 | 12/1991 |
| EP | 0 475 857 A1 | 3/1992 |
| EP | 0 475 857 B1 | 3/1992 |
| EP | 0 664 139 B1 | 7/1995 |
| EP | 0 830 871 B1 | 3/1998 |
| EP | 0 978 465 A1 | 12/2002 |
| FR | 2 263 789 | 3/1974 |
| WO | WO 90/03196 | 4/1990 |

(56) References Cited

FOREIGN PATENT DOCUMENTS

| | | |
|---|---|---|
| WO | WO 92/11885 | 7/1992 |
| WO | WO 95/24232 | 9/1995 |
| WO | WO 99/12594 B1 | 9/1998 |
| WO | WO 98/58584 | 12/1998 |
| WO | WO 99/12594 A1 | 3/1999 |
| WO | WO 00/06225 | 2/2000 |
| WO | PCT/US00/30822 | 2/2001 |
| WO | WO 01/08740 A1 | 2/2001 |
| WO | WO 01/36025 A1 | 5/2001 |
| WO | PCT/US00/30822 | 10/2001 |

OTHER PUBLICATIONS

Compact Oxford English Dictionary definition of "profile." http://www.askoxford.com/concise_oed/profile?view=uk.
EP Communication dated Mar. 7, 2012 with Supplementary Partial EP Search Report for EP Application No. 03785031.0 dated Feb. 10, 2012.
Compact Oxford English Dictionary definition of "profile" retrieved from http://www.askoxford.com/concise_oed/profile?view=uk, dated Sep. 30, 2006.

\* cited by examiner

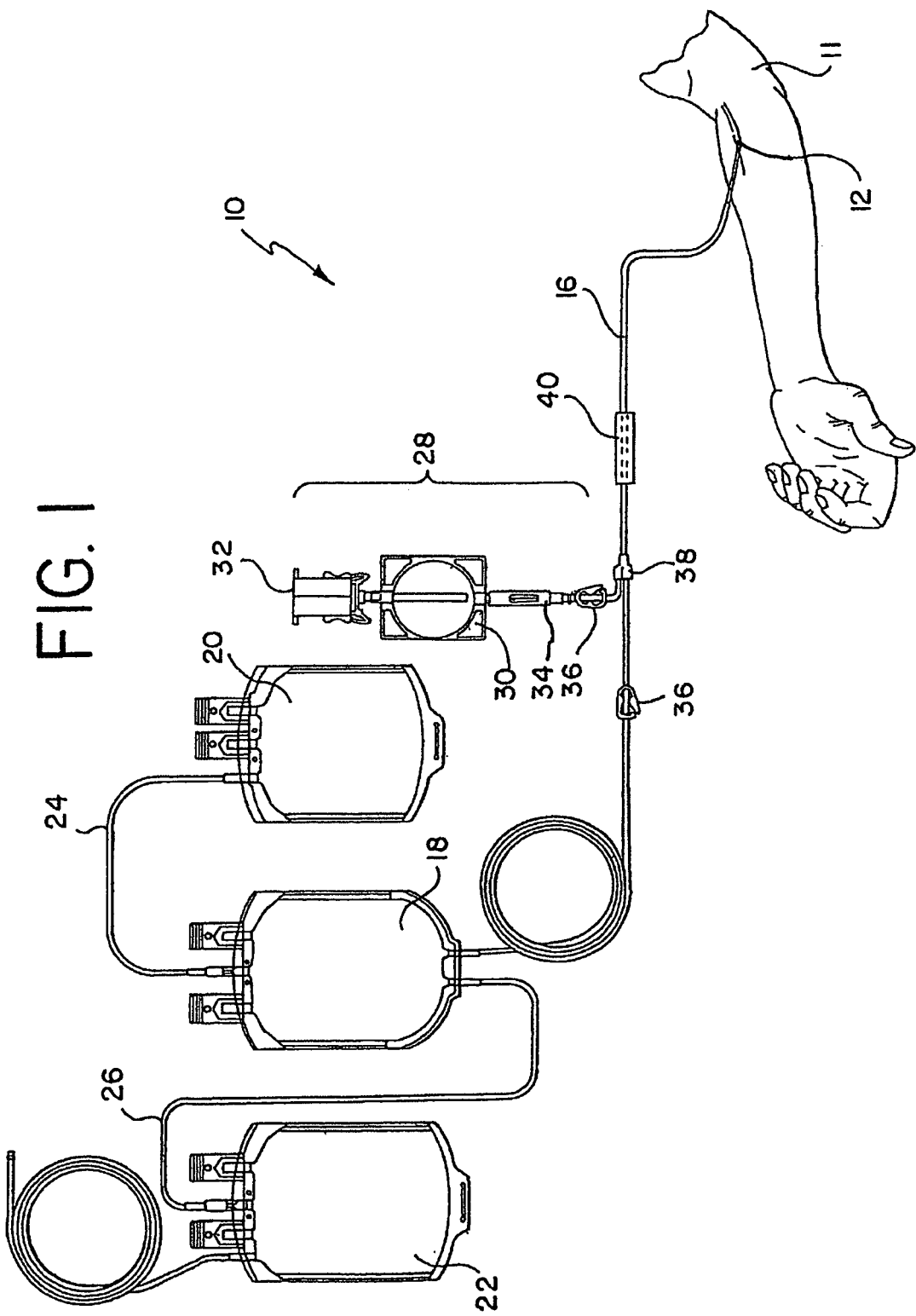

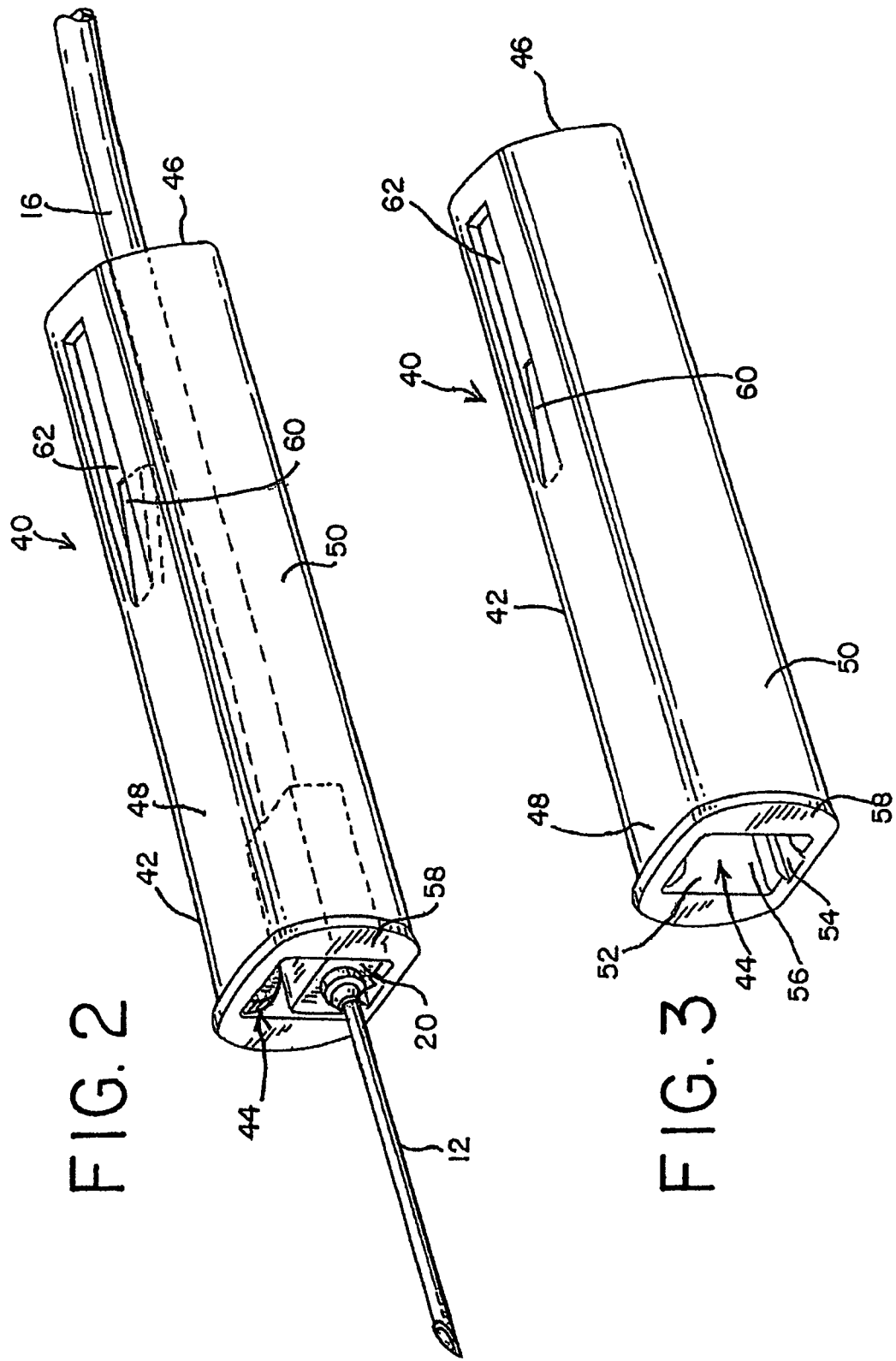

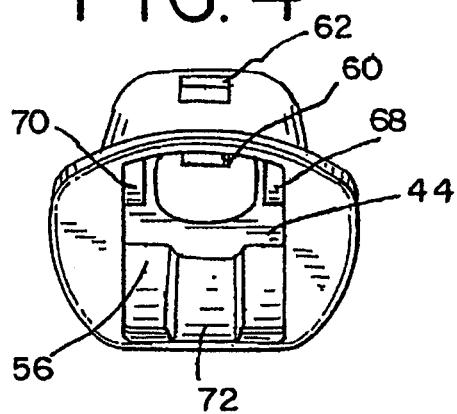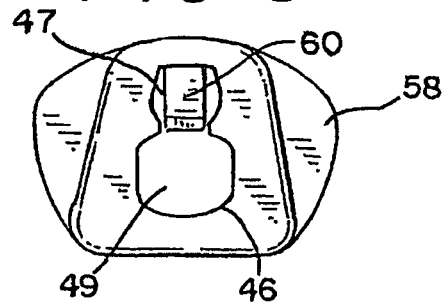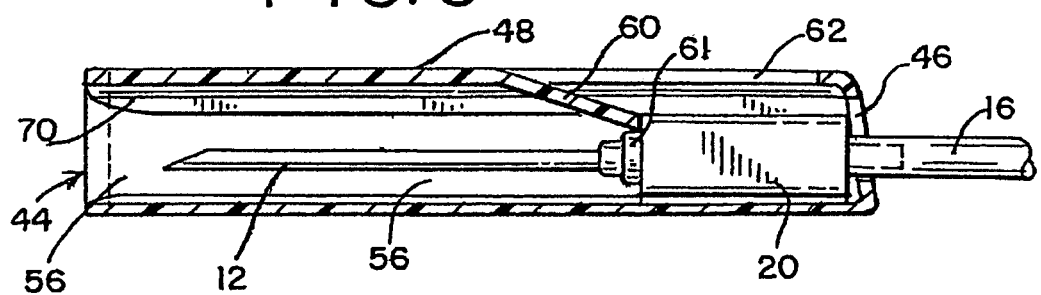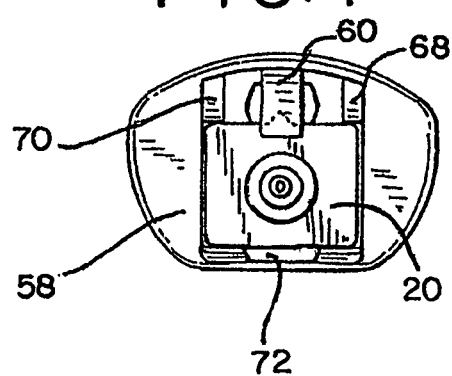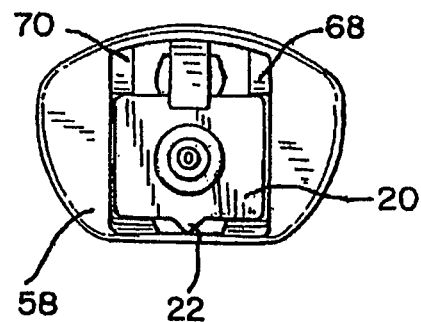

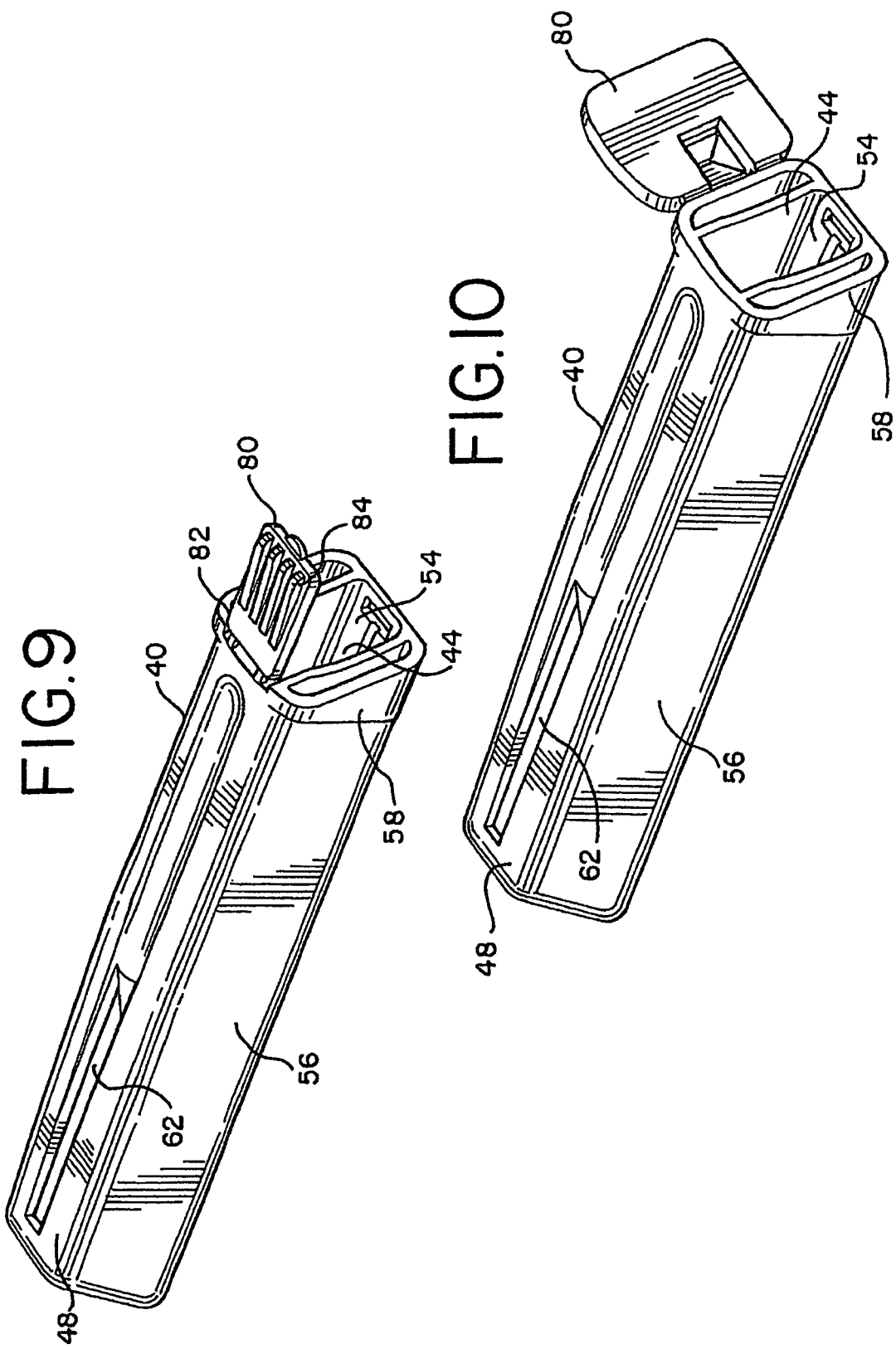

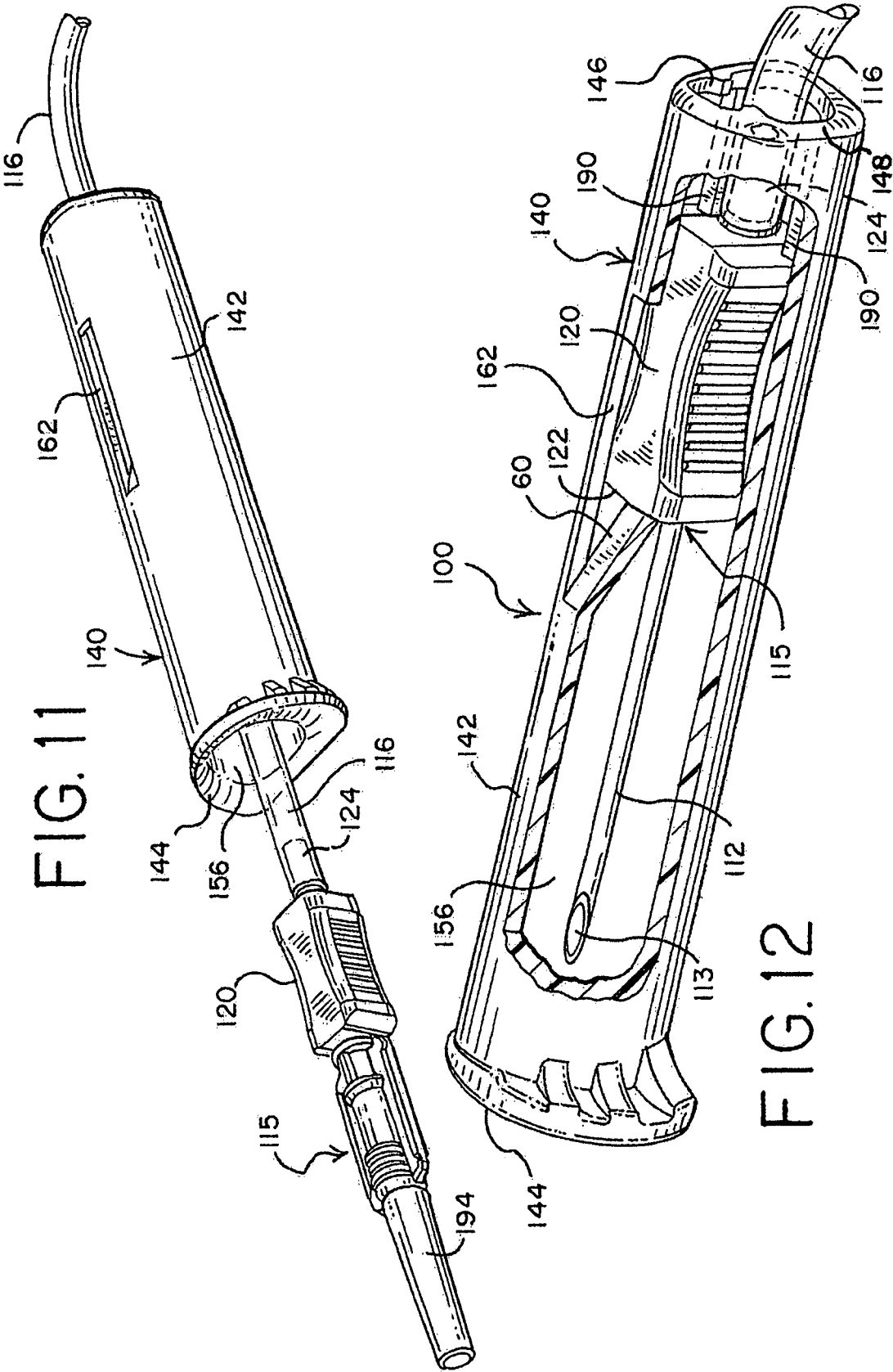

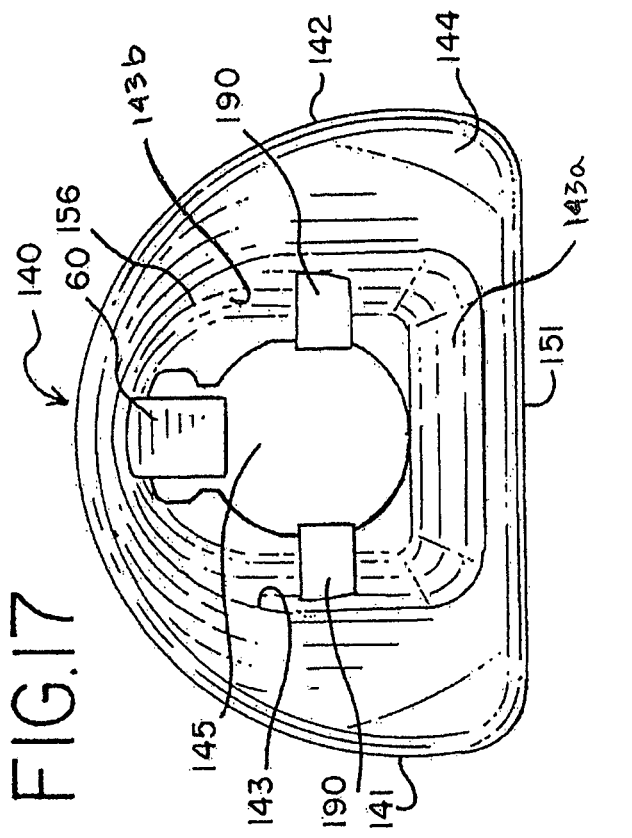
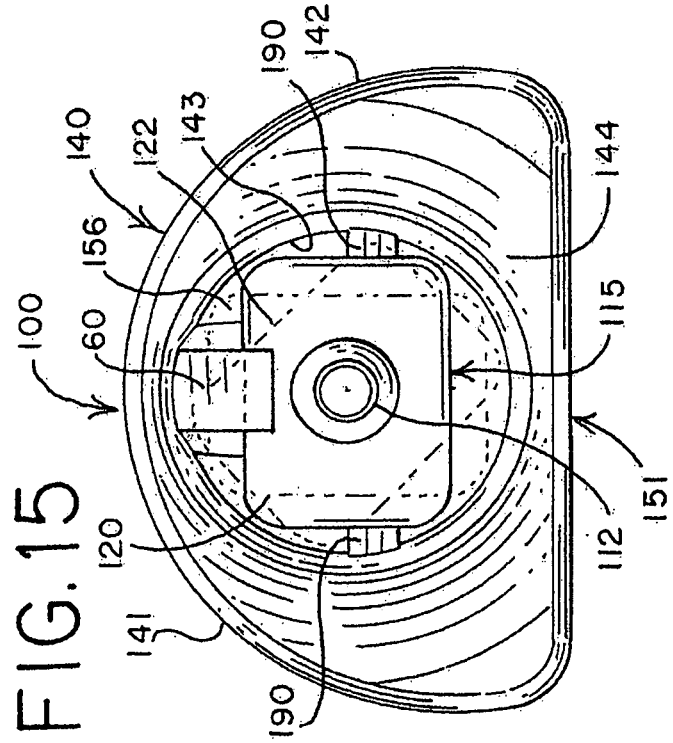
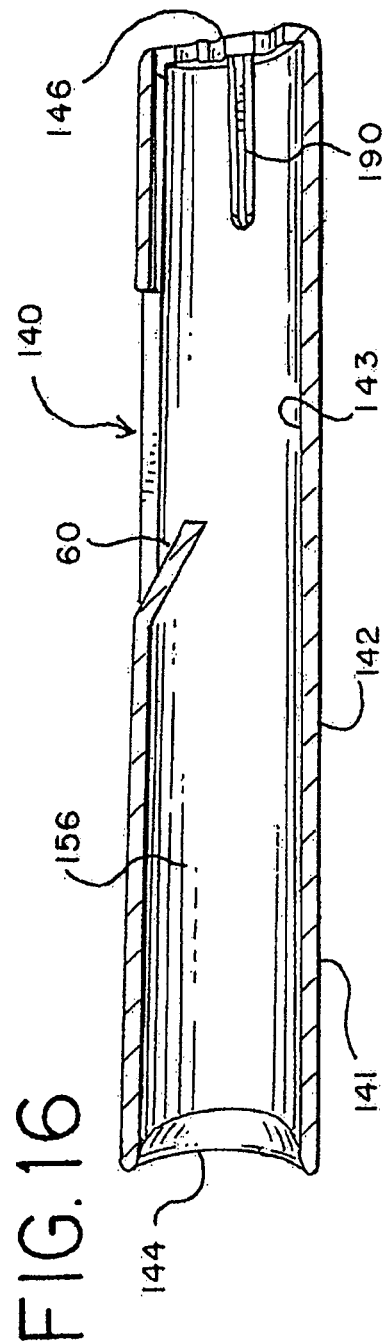

NEEDLE PROTECTOR, NEEDLE ASSEMBLY AND FLUID PROCESSING SET INCLUDING THE SAME

CROSS-REFERENCE TO RELATED APPLICATIONS

This application is a continuation-in-part of and claims priority to U.S. patent application Ser. No. 10/618,353, filed Jul. 11, 2003, now U.S. Pat. No. 7,566,327 which claims the benefit of U.S. Provisional Patent Application Ser. No. 60/402,286, filed Aug. 9, 2002, both of which are incorporated herein by reference.

BACKGROUND

The present disclosure is directed to protective devices (i.e., needle protectors) for use with medical needles to prevent inadvertent user contact with such needles.

Needle protectors are well known in the field of blood donation. Needle protectors are used to shield a used needle and, thereby, protect the medical personnel from an accidental needle stick.

Needle protectors are typically provided as part of a blood donation or collection kit, which includes a needle attached to one end of a needle hub. The other end of the need hub is attached to a length of plastic tubing that provides a flow path to one or more containers used to collect the donated blood. The needle protector is often provided as a sleeve placed over and/or around the plastic tubing. The plastic tubing extends through the needle protector, entering through one open end and exiting through an opposite open end.

After blood donation, the tubing is pulled by the medical technician to retract the needle and needle hub into the needle protector. The used needle is, thus, shielded from the medical technician.

U.S. Pat. Nos. 5,800,400, 6,042,570, and 6,165,157 are just a few of the many examples of known needle protectors. The needle protectors disclosed therein, and in other U.S. patents, include features to provide protection of medical personnel from accidental needle sticks. The needle protectors may also include features which prevent movement of the needle during blood donation, which could cause discomfort to the donor.

For example, U.S. Pat. No. 6,165,157 describes a needle protector that includes restraining means which restrain movement of the needle hub when the needle is inserted in the arm of the donor. The needle protector also includes locking means to secure the used needle in a completely shielded position after use.

While needle protectors such as those described above in the aforementioned patents have worked satisfactorily, efforts continue to provide a needle protector that assures the safety of the medical technician, is easy for the technician to manipulate and/or operate, and provides maximum comfort to the donor. Efforts continue to provide a needle protector that achieves these ends and combines them in a needle protector that is also easy and inexpensive to manufacture and easy to use by the medical personnel.

SUMMARY

The present disclosure is directed to a disposable biological fluid processing set including one or more containers. The disposable set also includes a needle assembly having a piercing end and a hub. Plastic tubing is attached to the needle assembly, providing a flow path from the needle assembly to one or more of the containers. A needle protector is associated with the plastic tubing. The needle protector has a body with first and second open ends. The body of the needle protector has an outer surface and an inner surface, the inner surface defining an interior chamber. A first open end of the body of the needle protector is sized and shaped to receive the needle hub of the needle assembly. The second open end of the body of the needle protector has an end wall defining a multiple profile window. The multiple profile window has a first relatively larger profile window and a second relatively smaller profile window that is adjacent to the first profile window.

The present disclosure is also directed to a needle and needle protector assembly. The needle assembly includes a piercing member with a piercing tip, a needle post and a needle hub associated with the needle post. Plastic tubing is attached to the needle post. The assembly also includes a needle protector. The needle protector has a body with first and second open ends. The body of the needle protector has an outer surface and an inner surface, the inner surface defining an interior chamber. The first open end of the body of the needle protector is sized and shaped to receive the needle hub of the needle assembly. The second open end of the body of the needle protector has an end wall defining a window sized such that the needle hub of the needle assembly cannot pass through the second open end. The window of the second open end is a multiple profile window including a first profile sized and shaped to allow the plastic tubing to slide through it and a second profile sized and shaped to at least temporarily retain the plastic tubing. The needle protector also includes a stop within the interior chamber adjacent to the second open end. In addition, a flexible retaining member extends from the inner surface of the body. The flexible retaining member is adapted to contact the needle hub and is spaced a sufficient distance from the first open end of the body such that when the needle hub is substantially retracted within the body the piercing end of the needle assembly is completely contained within the interior chamber.

BRIEF DESCRIPTION OF THE DRAWINGS

FIG. 1 is a plan view of a blood collection kit, including containers for collecting blood and a needle protector embodying the present invention;

FIG. 2 is a perspective view of the needle protector embodying the present invention in association with a needle assembly;

FIG. 3 is a perspective view of the needle protector embodying the present invention;

FIG. 4 is a front perspective view of the needle protector of FIG. 3;

FIG. 5 is a rear perspective view of the needle protector of FIG. 3;

FIG. 6 is a cross-sectional side view of the needle protector embodying the present invention in association with a needle assembly;

FIG. 7 is a front perspective view of the needle protector in combination with a needle assembly;

FIG. 8 is a front perspective view of the needle protector in combination with the needle assembly wherein the needle hub is rotated 180°;

FIG. 9 is a perspective view of one embodiment of the needle protector of the present invention including an end cap; and FIG. 10 is a perspective view of another embodiment of the needle protector of the present invention including an end cap;

FIG. 11 is a perspective view of another embodiment of a needle protector assembly of the present invention;

FIG. 12 is a cross-sectional perspective view of the needle protector assembly of FIG. 11 without a needle cover;

FIG. 15 is a front elevation view of the needle protector assembly of FIG. 12;

FIG. 16 is a side elevation cross-sectional view of the needle protector of FIG. 11;

FIG. 17 is a front elevation view of the needle protector only of the needle protector assembly of FIG. 15.

DETAILED DESCRIPTION

Figure 13:
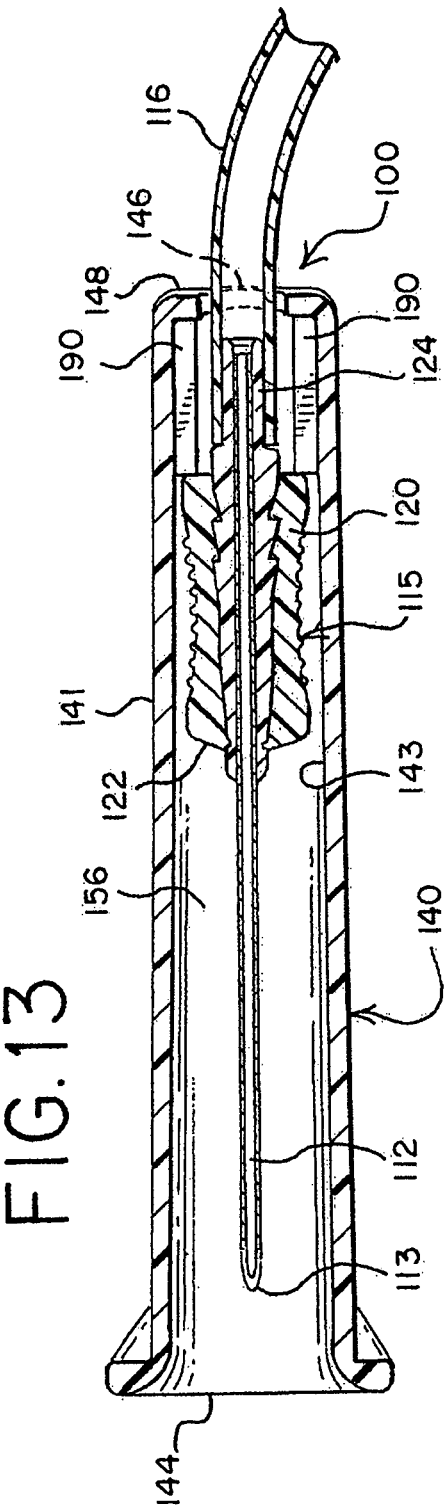
FIG. 13 is a top plan cross-sectional view of the needle protector assembly of FIG. 12.

The needle protector of the present invention will be described below in the context of its preferred use, namely, as a needle protector that is part of a disposable tubing and container set intended for the collection and processing of blood (or other biological fluid). It will be understood that the needle protector of the present invention is not limited to use with disposable tubing and container sets of the type shown in, for example, FIG. 1. In fact, the needle protector of the present invention may be used in any blood collection, donation, processing or treatment method and with any devices and tubing sets used for practicing such methods.

Also, as used herein, the term "needle" refers to any elongated member having a sharpened tip for puncturing or piercing. The term "needle" is not limited to traditional venipuncture needles, which are typically made of stainless steel and are relatively small in diameter. Although the term "needle" includes such venipuncture needles, it also includes piercing members made from other materials, such as plastic, and includes cannulas, coupling devices and the like.

Turning now to the drawings, FIG. 1 shows an exemplary disposable biological fluid processing set 10 for collecting blood from a donor 11. The illustrated disposable set 10 may include a needle, such as a venipuncture needle 12, and a plastic tubing segment 16 attached to needle 12 and extending from needle 12 to a plastic, blood collection container 18. Although not shown in FIG. 1, needle 12 may be attached to one end of a needle hub and tubing 16 is attached to the other end of a needle hub (as shown, for example, in FIG. 2).

The disposable blood processing set may include a single blood collection container 18, or more commonly, as shown in FIG. 1, may include a primary container and additional, integrally attached containers 20 and 22, as is well known in the field. The methods and disposable sets for practicing such methods are well known and will not be discussed here. They are described in U.S. Pat. Nos. 4,222,379, 5,445,629 and 6,387,086, all of which are incorporated by reference herein. As noted above, however, the needle protector of the present invention is not limited to use with such blood collection kits, but may also be used in connection with other apparatus and methods used in the processing, treatment and collection of blood or other biological fluid.

Also, shown in FIG. 1 is a needle protector 40 embodying the present invention. As shown in FIG. 1, needle protector 40 is placed on, around or otherwise associated with tubing 16, which leads from the venipuncture needle to one or more collection containers. More specifically, needle protector 40 provides a sleeve that is relatively moveable with tubing 16, as described in more detail below.

Turning now to FIG. 2, there is shown a needle protector 40 which includes a body 42 having an open distal end 44 and open proximal end 46 (best seen in FIG. 5). Open distal and proximal ends 44 and 46, respectively, are adapted and sized to receive tubing 16 of the blood tubing set 10. As shown, for example, in FIG. 2, distal end 44 includes a larger opening adapted for and of sufficient size to receive the needle hub 20. On the other hand, open proximal end 46 is sized so that hub 20 cannot exit through the proximal end 46. As shown in FIG. 5, open proximal end 46 may include a multi-profile window, including a portion 47 having a smaller diameter and a portion 49 having a larger diameter. The multi-profile window is discussed in greater detail below.

Returning now to FIGS. 2 and 3, needle protector 40, and specifically body 42, includes an outer surface and an inner surface between the proximal and distal open ends, the inner surface defining an interior chamber. The inner surface defining the interior chamber can be one continuous and preferably curved surface. Alternatively, the inner surface can include two or more adjacent surfaces, one or more of which may be generally flat. For example, in the illustrated embodiment of FIGS. 2 and 3, the body 42 includes a plurality of side walls 48, 50, 52 and 54. The outer surfaces of side walls define a needle protector body 42 with a generally rectangular shape. The inner surfaces of side walls 48, 50, 52 and 54 define an interior chamber 56 (FIG. 3) for receiving the needle assembly (i.e. needle 12, hub 20 and tubing 16). Of course, needle protector 40 can have any shape including, but not limited to, a cylindrical tube shape defined, for example, by a continuous arcuate wall.

As further seen in FIGS. 2 and 3, needle protector 40 may include retaining member 60 and a viewing slot 62. Preferably, retaining member 60 and viewing slot 62 are formed in top wall 48 near the proximal end 46 of needle protector 40.

Needle protector 40 may further include an outwardly extending flange 58 at the open distal end 44 of needle protector 40.

Turning now to FIGS. 4, 6, 7 and 8, in one embodiment needle protector 40 may also include guiding ledges 68 and 70. Guiding ledges 68 and 70 may be provided as outwardly extending lips that protrude from side walls 50 and 52 and/or depend downwardly from top wall 48. Guiding ledges 68 and 70 may span the entire length of the needle protector 40 from distal end 44 to proximal end 46. At the minimum, guiding ledges 68 and 70 may extend from distal end 44 substantially up to the proximal tip of retaining member 60. Guiding ledges 68 and 70 "guide" needle hub 20 as it is being retracted into needle protector 40 and prevent hub 20 from rotating once inside the needle protector 40. It will be appreciated that guiding ledges 68 and 70 are optional and are not included in other embodiments described below.

As further shown in FIGS. 4 and 8, needle protector 40 may include an optional longitudinal groove 72 in one of the side walls of the needle protector 40. Preferably, groove 72 extends substantially the entire length (from distal end 44 to proximal end 46) and is formed in bottom wall 54 of needle protector 40. In the event that hub 20 has been inverted 180° as it enters protector 40), groove 72 is provided to receive and accommodate rib 22 of hub 20. Groove 72 allows hub 20 to be retracted, even in the inverted position, into needle protector 40, without interference from guiding ledges 68 and 70. It will be appreciated that as with guiding ledges 68 and 70, groove 72 is optional and is not included in other embodiments described below.

It will be appreciated that the locations of guiding ledges of 68 and 70 and groove 72 may be inverted. For example, guiding ledges 68 and 70 may extend externally from side walls 50 and 52, but at a location closer to bottom wall 54. Conversely, groove 72 may be formed in top wall 48.

Turning now to FIG. 67 there is shown a needle protector assembly including a needle hub 20, a needle 12, (and a length of tubing extending from the one end of hub 20) fully retracted into needle protector 40. As shown in FIG. 6, retraction of hub 20 beyond retaining member 60 provides a locked and secured needle within needle protector 40. Full and complete retraction of the needle hub into the locked position is evidenced by an audible "click" sound caused by the snapping of retaining member 60 as hub 20 clears the proximal tip end 61 of retaining member 60. Retaining member 60 is sufficiently flexible and resilient such that it will not restrict movement of hub 20 in the direction of the proximal end 46 during retraction. Retaining member 60 may be a detent that extends downwardly from side wall 48 into interior chamber 56 in the direction of proximal end 46. Retaining member 60 may depend downwardly at an angle relative to sidewall 48. Retaining member 60 acts as a catch and prevents movement of hub 20 back out through open distal end 44. Whether the needle hub has been securely locked can also be ascertained by visual observation through viewing slot 62.

Turning now to FIG. 5, a multi-profile window in open proximal end wall 46 is provided to receive and at least temporarily retain tubing 16 of the blood tubing set 10. The multi-profile window allows for easy threading of tubing 16 through needle protector 40 during assembly of the kit. It also provides a means for more firmly holding the tubing when necessary. For example, when threading the tubing during assembly or when retracting the needle assembly into needle protector 40 after donation, the larger profile 49 is of a sufficiently large cross-section and therefore provides sufficient space to allow for easy retraction or movement of the tubing relative to needle protector 40. The smaller profile window 47 is of a smaller cross-section and may be used to secure the tubing and substantially prevent relative movement of the needle assembly and protector 40 during, for example, manufacture, shipping and/or blood donation. Specifically, tubing 16 may be press-fit into the smaller profile window 47 to at least temporarily to substantially prevent relative movement of the tubing and protector 40. Of course, during blood donation, relative movement of needle protector 40 and tube 16 may also be achieved by simply taping tubing 16 to the arm of the donor.

Needle protector 40 is preferably a unitary needle protector. By "unitary," it is meant that needle protector 40 is made of a single piece construction and is not made up of two or more joined or separable parts. Needle protector may be made by casting, or more preferably, injection molding, or by other means that will be known to those of skill in the art. Needle protector 40 may be made of any material that is suitably rigid and puncture resistant and suitable for use in the medical field. For example, needle protector 40 may be made of any thermoplastic material that can be sterilized by known sterilization techniques, including, but not limited to autoclaving, gamma radiation or electron beam radiation.

For example, needle protector 40 may be made of a polyolefin material, such as, most preferably, polypropylene. Other suitable materials may include polyethylene, such as high density polyethylene, polyacetal and polycarbonate. Of course, needle protector 40 may also be made of blends of two or more of the above-described materials. Preferably, the material used for needle protector 40 may be transparent to allow for viewing of the interior chamber of needle protector 40.

FIGS. 9 and 10 show the needle protector of the present invention including an end cap 80 attached to needle protector 40 at the distal end 44. Cap 80 may be attached to needle protector 40 by hinges attached to a sidewall of needle protector 40. In one embodiment, cap 80 may be attached to sidewall 48 (or 54). In another embodiment, cap 80 may be attached to either sidewall 50 or 52. Cap 80 may be attached to needle protector 40 and, specifically, sidewalls by a hinge(s) 82. Hinge 82 is preferably a living hinge which snaps cap 80 open or closed by a simple flick with a finger. This allows easy, one-handed operation of needle protector 40. Cap 80 may preferably be further provided with a lip 84. Lip 84 allows the technician to open and close cap 80 in the manner described above. Finally, cap 80 may also include gripping members 86 to provide some friction with the user's fingers when cap 80 is being closed.

Blood donation using a disposable processing set with the needle protector of the present invention begins with the technician disinfecting an area of the donor's arm. Needle 12 is then inserted into the vein at the disinfected area, with needle protector 40 slidably spaced from needle 12. While maintaining the needle in the inserted and correct position, the technician will slide needle protector 40 along tubing 16 toward needle 12 so as to partially enclose hub 20 within needle protector 40.

Typically, the technician will place a strip of adhesive tape over, for example, side wall 48 and adhere the ends of the tape to the donor's skin. This maintains needle protector 40 in place on the donor's arm during the blood donation. The technician may also, optionally, press tubing 16 into small profile window 47 or secure tube 16 to the donor's arm with tape, as previously described.

When donation is complete, the technician may withdraw needle 12 from the donor's arm by simply pulling tubing 16 with one hand while gently pressing down on needle protector 40 with the other hand. Needle 12 is retracted until needle hub 20 has passed retaining member 60 and a "click" is heard.

Once needle 12 has been firmly secured within protector 40, the technician will remove the tape and treat the punctured area of the donor's arm. Thus, needle protector 40 allows for smooth and easy retraction of the needle hub assembly from the donor when donation is completed, and minimizes the risk of accidental needle stick.

Turning now to FIGS. 11 through 16, the illustrated embodiment of a needle and needle protector assembly 100 includes a needle assembly 115 and a needle protector 140. Needle assembly 115 is generally described in U.S. patent application Ser. No. 12/412,626, which is incorporated herein by reference. As described therein and seen in FIG. 11-13, needle assembly 115 includes a cannula 112 terminating in a piercing distal tip 113. Cannula 112 is attached to a base or post 124 by, for example, overmolding post 124 over the proximal end of cannula 112, or by inserting cannula 112 into the bore of base 124 and securing the proximal end of cannula 112 to post 124 by, for example, an adhesive as described in U.S. patent application Ser. No. 12/912,626. As shown in FIG. 12, (and described in more detail in U.S. patent application Ser. No. 12/412,626), hub 120 includes an inner bore for receiving post 124. As shown in FIGS. 11-13, however, distal and proximal portions of post 124 may extend beyond hub 120. Proximal end of post 124 is adapted to form a liquid tight connection with tubing 116 of the fluid processing set 10.

As seen in FIGS. 11-13, a needle hub 120 may have a substantially rectangular cross-section with (e.g., concave) finger gripping surfaces on opposite sidewalls of hub 120. Of course, it will be appreciated that needle hub 120 is not limited to a substantially rectangular shape, but may be rounded, cylindrical or otherwise shaped.

As shown in FIG. 16, the illustrated embodiment of needle protector 140 has a body 142 with an outer surface 141 and an inner surface 143. Body 142 may be formed of a unitary single piece made of a substantially transparent or opaque plastic material. A surface (e.g., 151) of body 142 may be substantially flat (FIG. 15), allowing body 142 to, conform to a generally flat surface, such as an arm of a donor. Body 142 has an open distal end 144 sized and shaped to receive needle assembly 115 within an interior chamber 156. Open distal end 144 and interior chamber 156 are preferably sized and shaped such that needle hub 120 may be received in any radial orientation. That is, even if needle hub 120 is turned between 0 and 90 degrees relative to its intended horizontal orientation (as shown by broken lines in FIG. 15) during withdrawal of needle hub 120 into needle protector 140, distal open end 144 is large enough to receive needle hub 120 without restriction. In one embodiment, open distal end 144 and more particularly the opening or mouth in distal end 144 may be substantially circular, as shown in FIG. 15. The inside diameter of open distal end 144 is preferably greatest at the terminal end of body 142, but may gently and uniformly taper inward and thereby "blend" with the diameter of interior chamber 156. Alternatively, open distal end may have a non-circular or semi-circular profile. For example, as shown in FIG. 17, open distal and may have a profile of an upside-down "U" and curved inner surface 143b.

Figure 14:
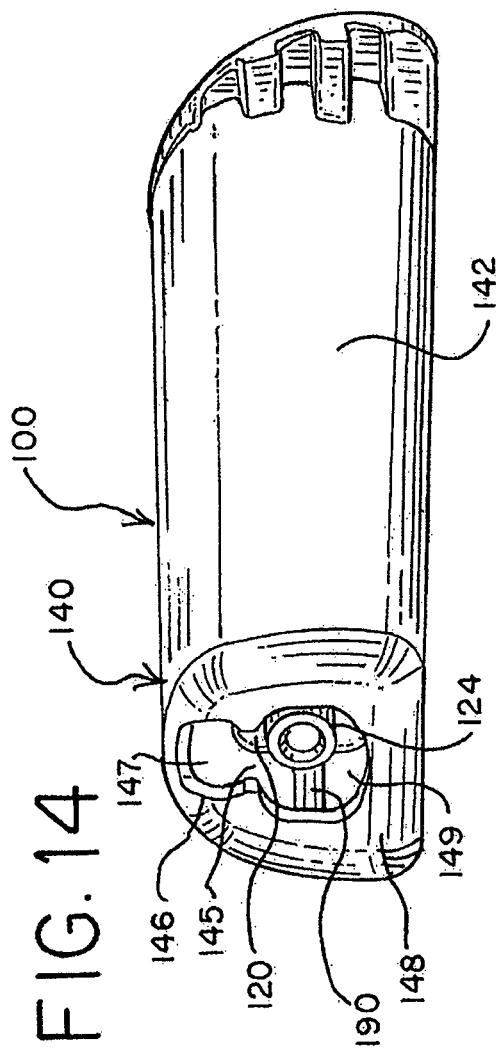
FIG. 14 is a rear perspective view of the needle protector assembly of FIG. 12.

As described above, at least a portion of interior chamber 156 may have a substantially circular cross-section as seen in FIG. 15. Alternatively, interior chamber 156 may have a non-circular or semi-circular shape or otherwise correspond to the profile of open distal end 144. Thus, for example, interior chamber 156 may be defined by one (or more) flat internal surfaces 143a and one (or more) curved surfaces 143b as seen in FIG. 17. Body 142 of needle protector 140 may also include a viewing slot 162 (FIG. 11) and as generally described above. Outer surface of body 142 at distal end 144 of needle protector 140 may be wider than the remainder of body 142. For example, distal end 144 of body 142 may be outwardly flared as shown in FIG. 13. Flared distal end 144 may be notched or ribbed as seen in FIG. 14, allowing for ease of gripping needle protector 140.

Body 142 has a proximal open end 146 that includes an end wall 148 having a multiple profile window as previously described. A multiple profile window 145 of the illustrated embodiment includes a smaller profile window 147 and a larger profile window 149 (FIG. 14).

As shown in FIG. 16, needle protector 140 may include a stop 190 within interior chamber 156 and, preferably, adjacent to proximal open end 146. Stop 190 is sized and shaped such that when needle hub 120 is in the fully retracted position, stop 190 is contacted by (or in near contact to) needle hub 120 thereby preventing further movement of hub 120 in the direction of the proximal open end 146. Preferably, stop 190 has a length that is greater than the portion of needle post 124 that extends beyond the proximal end of hub 120 so that needle post 124 is completely contained within interior chamber 156 (i.e., does not extend beyond end wall 148 and through window 145). Stop 190 may be an extended inner wall, one or more members or protrusions extending from proximal end wall 146, or one or more members extending from inner surface 143. In the illustrated embodiment shown in FIG. 13, stops 190 are provided as two ribs extending from inner surface 143 into interior chamber 156.

As shown in FIG. 12, needle protector 140 preferably includes a flexible retaining member 60 as previously described. After blood donation, needle assembly 115 is retracted into needle protector 140 beyond, flexible retaining member 60 (i.e., the fully retracted position). Movement of needle hub 120 from the fully retracted position in the direction of the distal end is prevented by contact with flexible retaining member 60 which would engages distal end wall 122. Flexible retaining member 60 is spaced a sufficient distance from end wall 148 such that distal tip 113 of needle cannula 112 is completely housed within interior chamber 156 and needle post 124 is fully contained within interior chamber 156 when hub 120 is in the fully retracted position.

As shown in FIG. 11, needle protector assembly 100 may further include a needle cover 194 that covers piercing member 112 during storage, shipping and handling for example. Needle cover 194 is typically removed immediately prior to use of needle protector assembly 100. In the illustrated embodiment shown in FIG. 11, needle cover 194 is frangibly attached to needle hub 120, as described in U.S. patent application Ser. No. 12/412,626, filed Mar. 27, 2009, which has been previously incorporated herein by reference.

While the present invention has been described in connection with the foregoing embodiments, it is to be understood that the invention is not limited thereto, but is intended to include various modifications and equivalent arrangements thereto.

That which is claimed:

1. A disposable biological fluid processing set comprising:
    one or more containers;
    a needle assembly comprising a piercing end and a hub having a distal end and a proximal end;
    a plastic tubing communicating with the needle assembly and providing a flow path from the needle assembly to the one or more containers; and
    a needle protector associated with the plastic tubing, the needle protector comprising:
        a body including proximal and distal open ends;
        the body having an outer surface and an inner surface, the inner surface defining an interior chamber;
        wherein the distal open end is sized and shaped to receive the hub;
        wherein the proximal open end comprises an end wall defining a dual-profile window consisting of a first window portion and a second window portion adjacent to said first window portion, wherein said second window portion is defined at least, in part, by a rounded profile and is smaller than said first window portion and is sized and shaped to allow said plastic tubing to be press-fit into said smaller second window portion and wherein said dual-profile window is entirely surrounded by said end wall; and
        a stop within said interior chamber and extending axially from an inner surface of said proximal end of said body toward said distal end of said body for contacting said proximal end of said hub and thereby preventing movement of said hub in a direction of said proximal end of said body.

2. The biological fluid processing set of claim 1 wherein the body of the needle protector comprises a wall including a flexible retaining member adapted for contacting the hub of the needle assembly, the flexible retaining member spaced from the distal end of said body such that when the hub is in a fully retracted position the piercing end is completely contained within the interior chamber.

3. The biological fluid processing set of claim 1 wherein the distal end of said body of the needle protector is outwardly flared.

4. The biological fluid processing set of claim 1 wherein the body of the needle protector defines a slot for viewing the interior chamber.

5. The biological fluid processing set of claim 1 wherein the needle protector comprises the body which is a unitary single piece of a plastic material that allows for viewing of the interior chamber.

6. The biological fluid processing set of claim 1 wherein the first window portion is sized to allow for free movement of the tubing therethrough.

7. A needle and needle protector assembly comprising:
a needle assembly including a piercing member terminating in a piercing distal tip and having a needle hub and a needle post wherein a portion of said needle post extends proximally beyond said needle hub, a plastic tubing attached to the needle post;
a needle protector for receiving said needle assembly in a retracted position, the needle protector comprising:
a body including proximal and distal ends, wherein said proximal and distal ends are open;
the body having an outer surface and an inner surface, the inner surface defining an interior chamber:
wherein the distal open end is sized and shaped to receive the needle hub;
wherein the proximal open end comprises an end wall, the end wall defining a window sized such that the needle hub cannot pass through the proximal open end, wherein said window is entirely surrounded by said end wall and consists of a first portion and a second portion, wherein said first and second portions are adjacent to each other and wherein the first portion is larger than the second portion;
a stop within the interior chamber adjacent to and extending from said end wall, wherein said stop is sized and positioned to contain said needle post portion that extends proximally from and beyond said needle hub within said interior chamber when said needle hub is in a fully retracted position; and
a flexible retaining member spaced from said stop and extending from the inner surface of the body, the retaining member adapted for contacting the needle hub and spaced from the distal end such that when the needle hub is in the fully retracted position the piercing distal tip is completely contained within the interior chamber.

8. The needle and needle protector assembly of claim 7, wherein at least a portion of the interior chamber is defined by one or more curved internal body surfaces.

9. The needle and needle protector assembly of claim 7, wherein said needle hub has concave finger-gripping surfaces.

10. The needle and needle protector assembly of claim 7, wherein the stop comprises a rib extending from the inner surface of the body.

11. The needle and needle protector assembly of claim 7, wherein the distal end of said body is flared.

12. The needle and needle protector assembly of claim 7, wherein the distal end is ribbed.

13. The needle and needle protector assembly of claim 7, wherein at least a portion of the outer surface of the body is flat.

14. The needle and needle protector assembly of claim 7, wherein a portion of the body defines a slot.

15. The needle and needle protector assembly of claim 7, comprising the body which is a unitary single piece.

16. The needle and needle protector assembly of claim 15, wherein the unitary single piece body is comprised of a plastic material that allows for viewing of the interior chamber.

17. The needle and needle protector assembly of claim 7, further comprising a needle cover completely enclosing the piercing distal tip.

18. The needle and needle protector assembly of claim 17, wherein the needle cover is frangibly attached to the needle hub.

19. The needle and needle protector assembly of claim 7 wherein said window is a dual-profile window consisting of the first portion having a profile sized and shaped to slidably receive the tubing and a the second portion having a profile sized and shaped to allow said plastic tubing to he press-fit into said second portion of said window and at least temporarily retain said tubing.

* * * * *